(12) United States Patent
Yohannes

(10) Patent No.: US 7,816,356 B2
(45) Date of Patent: Oct. 19, 2010

(54) ARYL AND HETEROARYLTETRAHYDRO-CYCLOBUTAPYRROLES AS NICOTINIC ACETYLCHOLINE RECEPTOR LIGANDS

(76) Inventor: Daniel Yohannes, 12 Salem St., Cambridge, MA (US) 02139

( * ) Notice: Subject to any disclaimer, the term of this patent is extended or adjusted under 35 U.S.C. 154(b) by 671 days.

(21) Appl. No.: 10/989,145

(22) Filed: Nov. 15, 2004

(65) Prior Publication Data

US 2005/0182063 A1 Aug. 18, 2005

Related U.S. Application Data

(60) Provisional application No. 60/520,126, filed on Nov. 14, 2003.

(51) Int. Cl.
*A61K 31/498* (2006.01)
*A61K 31/403* (2006.01)
(52) U.S. Cl. ...................... 514/250; 514/411
(58) Field of Classification Search ................ 514/411, 514/250; 548/427
See application file for complete search history.

(56) References Cited

U.S. PATENT DOCUMENTS 5,672,601 A 9/1997 Cignarella 6,630,491 B1 10/2003 Zoltewicz et al.

OTHER PUBLICATIONS

Decker et al. "The role of neuronal nicotinic acetylcholine receptors in antinociception: Effects of ABT-594" J. Physiology (Paris) 1998, 92, 221-224.*
News Release: "New drug may give smokers promising new option for kicking habit," Oct. 2, 2003, Massachusetts General Hospital, available at: http://www.mgh.harvard.edu/news/releases/100203smoking.html.
Quit Smoking News "Varenicline and the 7 Day Smoke Away," at http://www.smoke-away.info/quit-smoking-news.htm, accessed Oct. 24, 2003.
Roan, Shari, Los Angeles Times, "Quitting for Good," Oct. 20, 2003.
Drug Report: varencline tartrate, The Investigative Drugs Database, http://www.iddb3.com, accessed Oct. 24, 2003.

* cited by examiner

*Primary Examiner*—Sharmila Gollamudi Landau
*Assistant Examiner*—Kortney L Klinkel
(74) *Attorney, Agent, or Firm*—Burns & Levinson LLP; Yakov Korkhin; Janine M Susan

(57) ABSTRACT

Disclosed herein are compounds that bind to a neuronal nicotinic acetylcholine receptor. These compounds posses broad therapeutic use including the treatment of senile dementia, Alzheimer's disease, Parkinson's disease, attention deficit disorder, and the treatment of addictive disorders such as the use of tobacco in smoking or the use of other nicotine containing products. In addition, they have utility as cognitive enhancers, drug therapy for mental and neurological disorders related to a decrease in cholinergic function, for the treatment of obesity, Tourette's syndrome, or ulcerative colitis. Additionally, these compounds have utility as non-opioid analgesics for treatment of acute and chronic pain.

1 Claim, No Drawings

ARYL AND HETEROARYLTETRAHYDRO-CYCLOBUTAPYRROLES AS NICOTINIC ACETYLCHOLINE RECEPTOR LIGANDS

RELATED APPLICATIONS

This application claims priority to and the benefit of U.S. Provisional application 60/520,126, filed Nov. 14, 2003.

FIELD OF THE INVENTION

The present invention relates to pharmaceutical compositions, particularly pharmaceutical compositions that are capable of affecting nicotinic acetylcholine receptors (nAChRs). More importantly, the present invention relates to compounds capable of activating nAChRs, for example, as agonists or partial agonists of particular nAChR subtypes.

BACKGROUND OF THE INVENTION

It has long been customary in classifying diseases of the nervous system to group them as degenerative, thereby indicating they are characterized by a gradually evolving, relentlessly progressive, neuronal death. Science has shown that a considerable portion of disorders that are classed as degenerative are associated with genetic predisposition which results in a pattern of dominant or recessive inheritance. However, others, although they do not differ in a fundamental way from the hereditary disorders, may occur only sporadically as isolated instances within a given family.

As a consequence, since by definition, classification of degenerative diseases cannot be based upon exact knowledge of their cause or pathogenesis, subdivision of these diseases into individual syndromes rests upon descriptive criteria based largely upon pathologic anatomy and consideration of clinical aspects. As a result, this group of diseases presents itself in the form of several clinical syndromes. However, apart from the general differences that allows the distinction of one syndrome from another, there are certain general attributes which typify this entire class of disorders.

The degenerative diseases of the nervous system can typically be divided into disorders characterized by progressive dementia in the absence of other prominent neurologic signs.

In recent years, it has become evident that perturbation of nicotinic cholinergic neurotransmission can result in a number of neurodegenerative, neuropsychiatric and neurological disorders. Indications that may be serviced via therapy using nicotinic acetylcholine receptor (nAChR) ligands include Alzheimer's disease, Parkinson's disease, Tourette's syndrome, depression, attention deficit disorder (ADHD), schizophrenia, Lewy body dementia, acute and chronic pain, anxiety disorders, ulcerative colitis, and autosomal dominant nocturnal frontal lobe epilepsy (ADNFLE).

Nicotine has a wide variety of pharmacological effects. A number of compounds that affect the nAChRs are known to have utility for treating a wide variety of conditions and disorders.

While many neurological disorders are peripherally manifested, (e.g., ulcerative colitis), a large fraction of neurological disorders can be considered CNS disorders. A number of CNS disorders can be attributed to the disfunction of neurotransmitter systems such as dopamine, choline, norepinephrine, serotonin, etc. CNS disorders which may be classified as such include mild cognitive impairment, age-related cognitive decline, vascular dementia, presenile dementia (early-onset Alzheimer's disease), Alzheimer's disease, Parkinson's disease dementia, attention-deficit hyperactivity disorder, anxiety, dyslexia, schizophrenia, tardive dyskinesia, Tourette's syndrome, depression, and addiction.

Administration of an agonist or partial agonist of nAChRs to a patient suffering certain neurological disorders would provide a useful method for the treatment and/or prevention of those neurological disorders (e.g., CNS disorders). It would be desirable to provide patients suffering from CNS disorders related to deficiency of cholinergic transmission with a pharmaceutical composition which has nicotinic pharmacology and which has a beneficial effect on the disorder without significant adverse side effects. It is expected that a pharmaceutical composition incorporating a compound which interacts with neuronal nicotinic receptors as an agonist or partial agonist, when applied at amounts sufficient to affect functioning of the CNS, will not affect significantly those nicotinic receptor subtypes which have the potential to induce undesirable effects, for example, at skeletal muscle and ganglionic sites.

BRIEF SUMMARY OF THE INVENTION

The present invention relates to pharmaceutical compositions, particularly pharmaceutical compositions that are capable of affecting nicotinic acetylcholine receptors (nAChRs). More importantly, the present invention relates to compounds capable of activating nAChRs, for example, as agonists or partial agonists of particular nAChR subtypes.

One embodiment of the present invention relates to compounds having the formula (I)

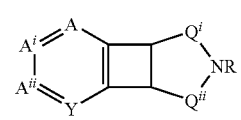

I wherein $Q^i$ is $(CH_2)_u$, and $Q^{ii}$ is $(CH_2)_v$, where u and v are independently 0, 1, 2, and 3; R is hydrogen or lower alkyl; and A, $A^i$, $A^{ii}$, and Y are independently nitrogen, nitrogen bonded to oxygen, or carbon bonded to hydrogen or a substituent species such as to represent a fused aromatic or heteroaromatic moiety.

One embodiment of the present invention is directed to aryltetrahydrocyclo-butapyrroles, and preferably to heteroaryltetrahydrocyclobutapyrroles. Of particular interest are quinoxalinotetrahydro-cyclobutapyrroles.

Another embodiment of the present invention is directed to pro-drug derivatives of the compounds in the present invention. The present invention also relates to methods for the synthesis of those types of compounds.

One embodiment of the present invention is directed to the administration of a therapeutically effective amount a compound of the present invention to a subject in need thereof.

For a better understanding of the present invention, together with other and further objects thereof, reference is made to the accompanying detailed description and its scope will be pointed out in the appended claims.

DETAILED DESCRIPTION OF THE INVENTION

The present invention relates to pharmaceutical compositions, particularly pharmaceutical compositions that are capable of affecting nicotinic acetylcholine receptors (nAChRs). More importantly, the present invention relates to compounds capable of activating nAChRs, for example, as agonists or partial agonists of particular nAChR subtypes.

The degenerative diseases of the nervous system can typically be divided into disorders characterized by progressive dementia in the absence of other prominent neurologic signs (e.g., Alzheimer's disease, senile dementia, and Pick's disease); syndromes which combine progressive dementia with other prominent neurologic abnormalities (e.g., Huntington's disease, Hallervorden-Spatz, and progressive familial myoclonic epilepsy); syndromes of gradually developing abnormalities of posture and movement (e.g., Parkinson's disease, striatonigral degeneration, torsion dystonia, and Gilles de la Tourette syndrome); syndromes of progressive ataxia (e.g., cerebellar cortical degeneration, olivopontocerebellar atrophy, and Friedreich's ataxia); and syndromes of muscular weakness and wasting without motor neuron disease (e.g., amyotrophic lateral sclerosis, spinal muscular atrophy, and hereditary spastic paraplegia), to name but a few. Among those diseases listed above, perhaps those most familiar are Alzheimer's and Parkinson's diseases. These diseases are progressive neurological disorders characteristically associated with aging. Alzheimer's disease is characterized by a profound loss of memory and other cognitive functions, while Parkinson's disease is an extrapyramidal movement disorder. Both are invariably fatal. Although there is no effective treatment for Alzheimer's disease, clinical trials are underway with several drugs that increase brain cholinergic transmission. In Parkinson's disease, several treatments are temporarily useful, notably L-DOPA related therapies that replace dopamine in the nigrostriatal pathway. However, in Parkinson's disease the therapeutic efficacy of even the best drugs is temporary at best.

Although the loss of neurons in the late stages of Alzheimer's disease is profound, only a few neuronal pathways appear to be affected in its earliest stages. These include cholinergic projections from the nucleus basalis to the cerebral cortex and from the septum to the hippocampus, noradrenergic projections from the locus cerululus to the cerebral cortex, and several peptidergic neurons that are probably intrinsic to the cerebral cortex. The loss of the aforementioned cholinergic pathways in particular is believed to underlie the early memory loss, since these pathways are known to be important for memory and cognition. This association accounts for the major emphasis in novel cholinergic treatments for Alzheimer's disease, at least in its early stages.

A recent study on Alzheimer's disease demonstrated that loss of cholinergic projections from the nucleus basalis to the cerebral cortex was sufficient, after extended intervals, to cause trans-synaptic neuron loss in the rat. Thus, it is conceivable that the early loss of analogous cholinergic neurons in Alzheimer's disease could cause a profound cascade phenomenon resulting in the loss of many neurons over a period of years. If so, then replacement therapy might not only improve survival of these neurons, but perhaps more important, keep other brain cells from dying.

Given the possibility of such therapy, it is of primary importance to determine the type of cholinergic agent most likely to improve memory and/or keep brain neurons from dying after the loss of cholinergic neurons. To address this issue, it is necessary to consider the two general types of cholinergic transmission in the brain. One is termed muscarinic, the other nicotinic. These terms are based on the type of receptor to which acetylcholine binds to in order to elicit its neurotransmitter effect. In brain regions associated with memory, the muscarinic receptors predominate quantitatively over the nicotinic receptors, although both types coexist. For this reason, most investigators traditionally focused on the development of muscarinic agonists to improve memory-related behaviors. These agents have been found to have moderate effects in rats with lesions of the nucleus basalis, but have little effect in patients with pronounced Alzheimer's disease.

Nicotinic transmission is also important for treating Alzheimer's disease. This is supported by the fact that cerebral cortical nicotinic receptors decrease significantly during the disease, while post-synaptic muscarinic receptor levels are often unchanged. These observations are consistent with the hypothesis that neurons expressing nicotinic receptors are lost in the disease. When these observations are combined with those of the present inventors, that lesions of ascending cholinergic neurons from the nucleus basalis cause a trans-synaptic neuron loss in the cortex, it is hypothesized that the neurons in the cortex that die trans-synaptically (and in Alzheimer's disease) do so because they do not receive enough nicotinic stimulation. For this reason, the inventor believes nicotinic agents are useful as replacement therapy for keeping brain neurons alive in Alzheimer's disease that would otherwise die from lack of nicotinic transmission. An analogous situation exists in several other systems such as: (a) muscle cells, which atrophy in the absence of nicotinic activation; (b) sympathetic ganglia, which require either nerve growth factor or nicotinic transmission (in the presence of calcium ions) in order to survive in culture; and (c) nigrostriatal dopamine neurons, which appear to be partially spared by nicotine following lesions of the substantia nigra. Also, it is important to note that there exist several types of nicotinic receptors in the brain, which allows considerable potential selectivity in targeting drugs for certain nicotinic sites.

The observation that nicotine treatment can preserve nigrostriatal dopamine neurons in an animal model for Parkinson's disease is consistent with epidemiological evidence that there is a lower incidence of this disease in cigarette smokers (even after adjusting for the smoking-induced increase in mortality). The mechanism whereby nicotine can preserve these neurons is not known, but it does appear to involve effects of nicotinic transmission on dopamine neurons themselves, since these neurons possess this type of cholinergic receptor. While the remainder of this patent application focuses on the potential treatment of Alzheimer's disease with nicotinic receptor agents, it should be noted that these drugs may be just as effective, or more so, on dopaminergic neurons that are lost in Parkinson's disease.

Nicotine has been used in several clinical trials for the treatment of Alzheimer's disease, primarily over rather short intervals for its potential memory enhancing effect (not for its ability to block long term trans-synaptic cell loss). In one recent study, nicotine had a marginally positive effect on memory and an even greater one of improving the mood of the patients. These positive results have not been followed up with longer term ones, however. Unfortunately, while nicotine has a history of improving memory related behaviors in humans and animals, its potent toxicity, low effective dose range, and peripheral side effects, have basically rendered it unacceptable for treating Alzheimer's disease.

One embodiment of the present invention is directed to compounds having the formula (I)

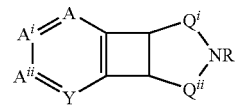

I wherein $Q^i$ is $(CH_2)^u$, and $Q^{ii}$ is $(CH_2)^v$ where u and v are independently 0, 1, 2, and 3; R is hydrogen or lower alkyl; and A, $A^i$, $A^{ii}$, and Y are independently nitrogen, nitrogen bonded to oxygen, or carbon bonded to hydrogen or a substituent species such as to represent a fused aromatic or heteroaromatic moiety.

In one aspect of the embodiment the compound of formula (I) is where R is hydrogen and $Q^i$ and $Q^{ii}$ are $CH_2$.

In another aspect of the present embodiment of the compound of formula (I) is where R is methyl and $Q^i$ and $Q^{ii}$ are $CH_2$.

In yet another aspect the compound of formula (I) is where R is hydrogen and $Q^i$ and $Q^{ii}$ are CH groups linked to each other with an ethyl ($CH_2CH_2$) bridge.

In still another aspect the compound of formula (I) is where R is methyl and $Q^i$ and $Q^{ii}$ are CH groups linked to each other with an ethyl ($CH_2CH_2$) bridge.

In a further aspect the compound of formula (I) is where A and Y are CH groups and $A^i$ and $A^{ii}$ are carbons attached to each other via a double bond and also fused to a second ring in the following manner: —N=$CR^1$=$CR^2$=N— to form a quinoxaline ring system.

Representative compounds of the present invention are those selected from a group consisting of:
a) 6-Methyl-2,3,3a,6,7,8b-hexahydro-1H-2,6-diaza-cyclopenta[3,4]cyclobuta[1,2-f]inden-5-one;
b) 2,3,3a,6,7,8b-Hexahydro-1H-2,6-diaza-cyclopenta[3,4]cyclobuta[1,2-f]inden-5-one;
c) 2,3,3a,5,7,8b-Hexahydro-1H-2,5,7-triaza-cyclopenta[3,4]cyclobuta[1,2-f]inden-6-one;
d) 5,6-difluoro-2,3,3a,7b-tetrahydro-1H-benzo[3,4]cyclobuta[1,2-c]pyrrole;
e) 6-Fluoro-2,3,3a,7b-tetrahydro-1H-benzo[3,4]cyclobuta[1,2-c]pyrrole-5-carbonitrile;
f) 5-ethynyl-6-fluoro-2,3,3a,7b-tetrahydro-1H-benzo[3,4]cyclobuta[1,2-c]pyrrole;
g) 6-Ethynyl-2,3,3a,7b-tetrahydro-1H-benzo[3,4]cyclobuta[1,2-c]pyrrole-5-carbonitrile;
h) 2,3,3a,7b-tetrahydro-1H-benzo[3,4]cyclobuta[1,2-c]pyrrole;
i) 5-Fluoro-2,3,3a,7b-tetrahydro-1H-benzo[3,4]cyclobuta[1,2-c]pyrrole;
j) 5-methyl-2,3,3a,7b-tetrahydro-1H-benzo[3,4]cyclobuta[1,2-c]pyrrole;
k) 5-Trifluoromethyl-2,3,3a,7b-tetrahydro-1H-benzo[3,4]cyclobuta[1,2-c]pyrrole;
l) 5-nitro-2,3,3a,7b-tetrahydro-1,4-benzo[3,4]cyclobuta[1,2-e]pyrrole;
m) 5-Methyl-1,2,3,3a,5,8b-hexahydro-2,5,7-triaza-cyclopenta[3,4]cyclobuta[1,2-f]indene;
n) 6-methyl-1,2,3,3a,5,8b-hexahydro-2,5,7-triaza-cyclopenta[3,4]cyclobuta[1,2-f]indene;
o) 6-Methyl-5-phenyl-1,2,3,3a,5,8b-hexahydro-2,5,7-triaza-cyclopenta[3,4]cyclobuta[1,2-f]indene;
p) 6,7,8,8a-tetrahydro-5bH-pyrrolo[3',4':3,4]cyclobuta[1,2-g]quinoxaline;
q) 7-methyl-6,7,8,8a-tetrahydro-5bH-pyrrolo[3',4':3,4]cyclobuta[1,2-g]quinoxaline;
r) 2,3-dimethyl-6,7,8,8a-tetrahydro-5bH-pyrrolo[3',4':3,4]cyclobuta[1,2-g]quinoxaline;
s) 2,3,7-trimethyl-6,7,8,8a-tetrahydro-5bH-pyrrolo[3',4':3,4]cyclobuta[1,2-g]quinoxaline;
t) 2,3,3a,8b-Tetrahydro-1H-5-oxa-2,7-diaza-cyclopenta[3,4]cyclobuta[1,2-f]indene;
u) 6-Methyl-2,3,3a,8b-tetrahydro-1H-5-oxa-2,7-diaza-cyclopenta[3,4]cyclobuta[1,2-f]indene;
v) 5-chloro-2,3,3a,7b-tetrahydro-1H-benzo[3,4]cyclobuta[1,2-c]pyrrole;
w) 2,3,3a,7b-Tetrahydro-1H-benzo[3,4]cyclobuta[1,2-c]pyrrole-5-carbonitrile;
x) 1-(2,3,3a,7b-Tetrahydro-1H-benzo[3,4]cyclobuta[1,2-c]pyrrol-5-yl)-ethanone;
y) 2,3,3a,7b-Tetrahydro-1H-benzo[3,4]cyclobuta[1,2-c]pyrrol-5-ol;
z) 7-Methyl-2,3,3a,8b-tetrahydro-1H-5-oxa-2,6-diaza-cyclopenta[3,4]cyclobuta[1,2-f]indene; and
aa) 5,6-Dichloro-2,3,3a,7b-tetrahydro-1H-benzo[3,4]cyclobuta[1,2-c]pyrrole.

The manner in which the compounds of the present invention (aryl and heteroaryltetrahydrocyclobutapyrroles) are synthetically made can vary. The compounds and processes of the present invention will be better understood in connection with the following synthetic schemes which illustrate the methods by which the compounds of the invention can be prepared. The groups, A, $A^i$, $A^{ii}$, Y, $Q^i$, $Q^{ii}$ and R as defined above unless otherwise noted.

SCHEME I

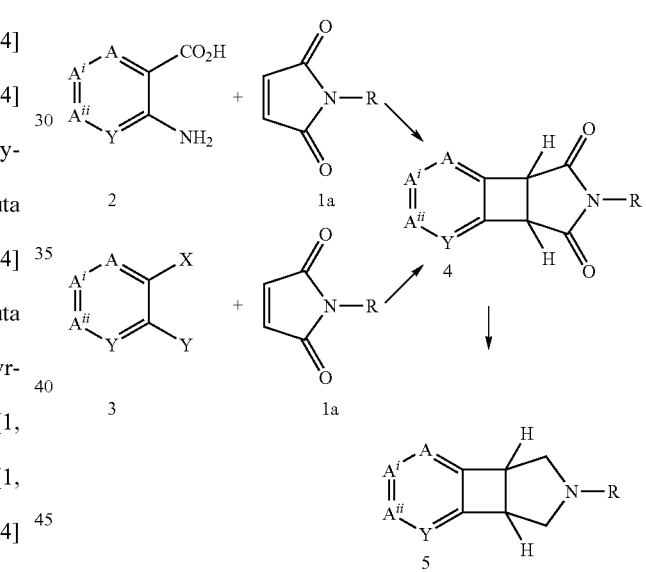

In accordance with Scheme I, the compounds of formula (I) can be prepared directly from their 2-amino aryl carboxylates via 2+2 cyclo-addition reactions resulting from diazotization if anthranilic acid derivatives or 1,2-dihalo derivatives with a suitable basic reagent like NaOH to generate an "in situ" benzyne species followed by reaction with an N-substituted maleimide; the isolated maleimide cycloadduct is then reduced by a reducing agent like LAH. Another source of the benzyne species may be the dihaloaryl derivates, as shown in Scheme I, wherein the reagent that generates the benzyne may be a stronger base such as a Grignard reagent. Those skilled in the art will recognize that when R is benzyl or a substituted benzyl group, it can be replaced with other alkyl groups by treatment under hydrogenation or other reduction methods in the presence of excess alkyl halide in alcohol. Those skilled in the art will also recognize that when R is benzyl or a substituted benzyl group, it can be replaced with hydrogen under hydrogenation protocols.

SCHEME II

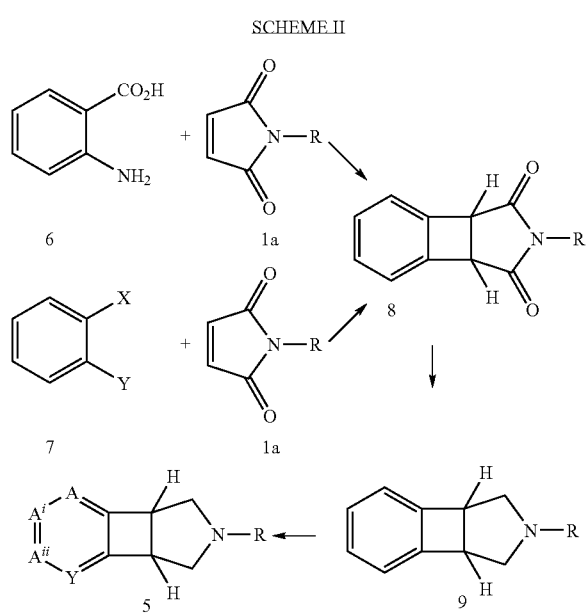

Alternatively, as shown in Scheme II, compounds of formula (I) can be accessed from similar processes to Scheme I on anthranilic acid itself or on a dihalobenzene such as 2-fluorobromobenzene or 1,2-difluorobenzene, followed by derivatization of the trycylic system. As in scheme I, R can be replaced with a number of alkyl groups or with hydrogen using methods known in the art.

SCHEME III

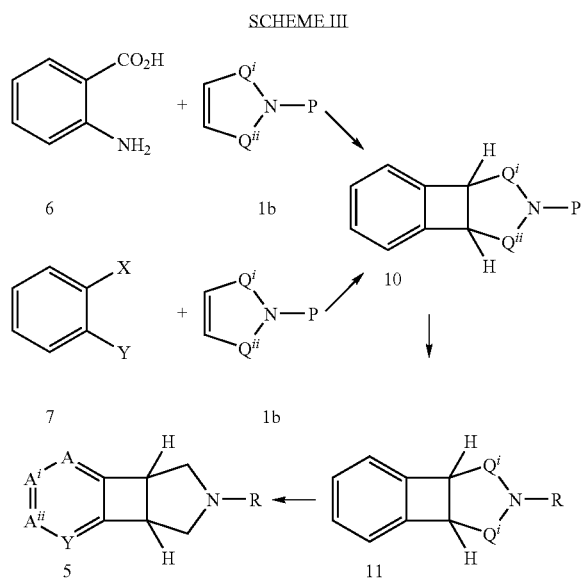

In another form of this approach, in accordance with Scheme III, compounds of formula (I) can be prepared via the 2+2 cycloaddition from either of two different sources of benzyne and a pyrroline derivative such as 1b. Those skilled in the art will also recognize that the pyrroline derivative 1b may also take the form of a bicyclic species 7-azanorbornene where $Q^i$ and $Q^{ii}$ are tethered through a $CH_2CH_2$ linker. In this approach, P can be a benzyl or substituted benzyl group which can be removed under reductive conditions. P can also be a basic-Nitrogen protecting group, such as Boc or Z-group, which can be removed under acidic or hydrogenolysis conditions. The Nitrogen can then be alkylated using methods known in the art, such as treatment with alkyl halides or reductive amination using alkyl aldehydes and a common reducing agent like $NaBH_4$ or $NaCNBH_3$ or $Na(OAc)BH_3$.

The invention also is directed to methods for administering a therapeutically effective amount of a compound of the present invention to a subject in need thereof.

The term "therapeutically effective" means that the amount of nicotinic receptor agent used is of sufficient quantity to increase brain cholinergic transmission. The dosage ranges for the administration of the agent of the invention are those large enough to produce the desired effect in which the nicotinic receptors show some degree of stimulation. The dosage should not be so large as to cause adverse side effects, such as unwanted cross-reactions, anaphylactic reactions, and the like. Generally, the dosage will vary with the age, condition, sex, and extent of the disease in the patient and can be determined by one of skill in the art. The dosage can be adjusted by the individual physician in the event of any contraindications. Dosage can vary from about 1 µg/kg/dose to about 1000 µg/kg/dose, preferably from about 10 µg/kg/dose to about 500 µg/kg/dose, most preferably from about 30 µg/kg/dose to about 100 µg/kg/dose in one or more dose administrations daily, for one or several days. Alternatively, the dosage can be administered indefinitely in order to prevent a recurrence of cognitive function loss, for example, by administration of the agent in a slow-release form.

The nicotinic receptor agent of the invention can be administered enterally, parenterally, or by gradual perfusion over time. The nicotinic receptor agent of the invention can be administered intravenously, intraperitoneally, intramuscularly, subcutaneously, intracavity, transdermally, or orally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose, and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. In order to form a pharmaceutically acceptable composition suitable for effective administration, such compositions will contain an effective amount of the nicotinic receptor agent, together with a suitable amount of a carrier vehicle. Additional pharmaceutical methods may be employed to control the duration of action. Controlled release preparations may be achieved by the use of polymers to complex or adsorb the nicotinic receptor agent. The controlled delivery may be exercised by selecting appropriate macromolecules (for example, polyesters, polyamino acids, polyvinyl pyrrolidone, ethylenevinylacetate, methylcellulose, carboxymethylcellulose, and protamine sulfate) and the concentration of macromolecules as well as the methods of incorporation in order to control release. Another possible method to control the duration of action by controlled release preparations is to incorporate the nicotinic receptor agent into particles of a polymeric material such as polyesters, polyamino acids, hydrogels, poly (lactic acid) or ethylene vinylacetate copolymers. Alternatively, instead of incorporating the nicotinic receptor agent into these polymeric particles, it is possible to entrap the nicotinic receptor agent in microcapsules prepared, for example, by coacervation techniques or by interfacial polymerization, for example, hydroxymethylcellulose or gelatin-microcapsules and poly (methylmethacrylate) microcapsules, respectively, or in colloidal drug delivery systems, for example, liposomes, albumin microspheres, microemulsions, nanoparticles, and nanocapsules or in macroemulsions. Such teachings are disclosed in Remington's Pharmaceutical Sciences (17th Ed., A. Oslo, ed., Mack, Easton, Pa., 1985, the teachings of which incorporated herein in its entirety).

The invention also relates to a method for preparing a medicament or pharmaceutical composition comprising the nicotinic receptor agent of the invention, the medicament being used for therapy to stimulate brain cholinergic transmission.

Although the invention has been described with respect to various embodiments, it should be realized this invention is also capable of a wide variety of further and other embodiments within the spirit and scope of the appended claims.

The invention claimed is:

1. A pharmaceutical composition comprising a compound selected from the group consisting of:
   h)  2,3,3a,7b-tetrahydro-1H-benzo[3,4]cyclobuta[1,2-c]pyrrole;
   l)  5-nitro-2,3,3a,7b-tetrahydro-1H-benzo[3,4]cyclobuta[1,2-c]pyrrole;
   p)  6,7,8,8a-tetrahydro-5bH-pyrrolo[3',4':3,4]cyclobuta[1,2-g]quinoxaline;
   r)  2,3-dimethyl-6,7,8,8a-tetrahydro-5bH-pyrrolo[3',4':3,4]cyclobuta[1,2-g]quinoxaline;
   v) 5-chloro-2,3,3a,7b-tetrahydro-1H-benzo[3,4]cyclobuta[1,2-c]pyrrole.

* * * * *